United States Patent
Huh et al.

(10) Patent No.: US 7,901,633 B2
(45) Date of Patent: Mar. 8, 2011

(54) QUANTITATIVE CELL DISPENSING APPARATUS USING LIQUID DROP MANIPULATION

(75) Inventors: Nam Huh, Seoul (KR); Jeong-gun Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 1126 days.

(21) Appl. No.: 11/491,825

(22) Filed: Jul. 24, 2006

(65) Prior Publication Data

US 2007/0148763 A1 Jun. 28, 2007

(30) Foreign Application Priority Data

Dec. 22, 2005 (KR) .................. 10-2005-0127795

(51) Int. Cl.
  *B01L 3/02* (2006.01)
  *G01N 1/10* (2006.01)
(52) U.S. Cl. ..... 422/100; 436/180; 422/68.1; 73/863.32; 73/864
(58) Field of Classification Search .................. 422/100, 422/68.1; 436/180; 73/863.32, 864; 204/600, 204/604
  See application file for complete search history.

(56) References Cited

U.S. PATENT DOCUMENTS

| | | | | |
|---|---|---|---|---|
| 5,601,980 | A * | 2/1997 | Gordon et al. ............... | 435/6 |
| 6,284,113 | B1 * | 9/2001 | Bjornson et al. ............. | 204/453 |
| 6,569,385 | B1 * | 5/2003 | Little et al. ................. | 422/100 |
| 6,620,620 | B1 * | 9/2003 | Anderson et al. ............ | 436/55 |
| 7,160,512 | B2 * | 1/2007 | Hirota et al. ................ | 422/100 |
| 7,226,788 | B2 * | 6/2007 | De La Torre-Bueno ........ | 436/46 |
| 7,442,502 | B2 * | 10/2008 | Hirota et al. ................ | 435/6 |
| 7,667,194 | B2 * | 2/2010 | Noritake et al. .............. | 250/284 |
| 2004/0055536 | A1 | 3/2004 | Kolar et al. | |

OTHER PUBLICATIONS

"An Investigation of Electrowetting-Based Microactivation", Jul./Aug. 1990, Colgate, Matsumoto: J. Vac. Sci. Technol. A vol. 8#4 p. 3625-3633.
"Electrostatic Activation of Liquid Droplets for Microreactor Applications", Jul./Aug. 1998, Washizu: IEEEtrans. on Ind. App. v. 34, #4, pp. 732-737.

* cited by examiner

*Primary Examiner* — Brian R Gordon
(74) *Attorney, Agent, or Firm* — Cantor Colburn LLP (57) ABSTRACT

Provided is a quantitative cell dispensing apparatus using liquid droplet manipulation, for quantitatively dispensing cells from hydrophilic suspension containing a plurality of cells. The quantitative cell dispensing apparatus includes hydrophilic suspension, a liquid droplet manipulation unit, a dispensing unit, a sensing unit, and a control unit. The hydrophilic suspension includes a plurality of cells and electrolyte, and the liquid droplet manipulation unit. The liquid droplet manipulation unit includes an inlet and a liquid droplet outlet portion. The dispensing unit discharges a liquid droplet received from the liquid droplet outlet portion to a target portion. The sensing unit optically senses liquid droplets distributed on a panel of the liquid droplet manipulation unit. The control unit analyses the number of cells contained in each liquid droplet using a single sensed by the sensing unit, and controls the liquid droplet manipulation unit to transfer a liquid droplet containing a predetermined number of cells to the liquid droplet outlet portion.

31 Claims, 9 Drawing Sheets

SAMPLE 1

FIG. 10B

SAMPLE 2

QUANTITATIVE CELL DISPENSING APPARATUS USING LIQUID DROP MANIPULATION

CROSS-REFERENCE TO RELATED PATENT APPLICATION

This application claims the benefit of Korean Patent Application No. 10-2005-0127795, filed on Dec. 22, 2005, in the Korean Intellectual Property Office, the disclosure of which is incorporated herein in its entirety by reference.

BACKGROUND OF THE INVENTION

1. Field of the Invention

The present invention relates to an apparatus for dispensing a predetermined amount of cells contained in a hydrophilic suspension, and more particularly, to an apparatus for dispensing a predetermined amount of cells by analyzing the number of cells contained in the liquid droplet while manipulating a liquid droplet of a hydrophilic suspension using an electrowetting-based liquid droplet manipulation unit. The present invention may be used for dispensing a predetermined amount of cells required for manufacturing of a cell chip, or dispensing a predetermined amount of minute particles dispersed in a hydrophilic liquid.

2. Description of the Related Art

Generally, a cell chip means a microchip used for fixing cells such as bacteria, animal cells on a surface of a solid substrate made of silicon, surface-modified glass, polypropylene, or activated polyacrylamide, and analyzing various reaction patterns such as gene expression patterns, genetic defects, and protein generation. Since a complicated physiological signal from a cell that has not been measured by a conventional method can be detected through real-time reaction of a living cell, microchip is very useful.

To manufacture a cell chip, dispensing a predetermined amount of cells is required. To manufacture a cell chip of high integration, a very small amount of a suspension droplet is dispensed onto a narrow region on a substrate because uniformity in the number of cells contained in this minute liquid droplet is required. A variety of methods and apparatuses have been proposed to dispense, in a minute liquid droplet, suspension of a bio material such as deoxyribo nucleic acid (DNA), protein, and animal cells. However, a constant volume of a minute liquid droplet does not necessarily mean that bio materials contained in the minute liquid droplet is dispensed by a constant amount.

Particularly, when cell suspension is dispensed, a particle (cell) size is large and so it is difficult to uniformly disperse cells inside the suspension. Accordingly, the number of the cells contained in a liquid droplet cannot be controlled. Also, as time elapses, the cells contained in the suspension easily cohere and viscosity of the suspension changes, which makes it more difficult to dispense a liquid droplet by a constant volume, and a deviation in the number of cells contained in each liquid droplet increases. To uniformly disperse the cells inside the suspension, a method of reducing the number of cells per unit volume, i.e., density of cell suspension may be considered. However, when density is reduced to about $10^5$ cells/ml ($=10^{-4}$ cell/pl), 10,000 times of dispensing should be performed in order to dispense by 1 pl and obtain a liquid droplet containing one cell. Accordingly, efficiency remarkably decreases when a cell chip is manufactured.

Therefore, an apparatus capable of dividing cell suspension into minute liquid droplets, and simultaneously, quantitatively dispensing the liquid droplets such that a desired number of cells are contained in each liquid droplet, is highly required.

SUMMARY OF THE INVENTION

The present invention provides an apparatus for dispensing suspension containing cells into liquid droplets of a minute volume using an electrowetting-based liquid drop manipulation unit, and simultaneously, analyzing the number of cells contained in each liquid droplet using an optical sensor to allow a predetermined amount of cells to be contained in each liquid droplet, and discharging the liquid droplet containing the predetermined amount of cells toward a target portion.

According to an aspect of the present invention, there is provided a quantitative cell dispensing apparatus using liquid droplet manipulation, the apparatus including: a hydrophilic suspension containing a plurality of cells and to which electrolyte is added; a liquid droplet manipulation unit manipulating a liquid droplet of the hydrophilic suspension on an electrode array consisting of a plurality of electrode pads using electrowetting, and having an inlet through which the hydrophilic suspension is supplied and at least one liquid droplet outlet portion discharging the manipulated liquid droplet; a dispensing unit discharging a liquid droplet received from the liquid droplet outlet portion to a target portion; a sensing unit optically sensing liquid droplets distributed on a panel of the liquid droplet manipulation unit; and a control unit analyzing the number of cells contained in each liquid droplet using a signal detected by the sensing unit and controlling the liquid droplet manipulation unit to provide liquid droplets containing a predetermined number of cells to the liquid droplet outlet portion through dividing, transferring, and merging the liquid droplets.

The liquid droplet manipulation unit may include: a lower substrate; the electrode array located on the lower substrate and having a plurality of electrode pads electrically isolated from each other, the plurality of electrode pads including at least one liquid droplet outlet pad; a first film located on a surface of the electrode array and having insulation property and hydrophobicity; a transparent upper substrate facing the upper surface of the lower substrate, and located substantially in parallel to the lower substrate such that a predetermined space is provided between the lower substrate and the upper substrate; a transparent electrode located on a lower surface of the upper substrate; a second film provided on a surface of the transparent electrode to contact the predetermined space and having transparency and hydrophobicity; a non-polar fluid filling the predetermined space; and an electrode selection portion connected to each of the plurality of electrode pads, and selecting some of the electrode pads of the electrode array according to a control signal to apply a predetermined voltage thereto.

The dispensing unit may include: a receiving portion connected with the liquid droplet outlet pad to receive a liquid droplet containing a predetermined amount of cells; and a dispensing port provided vertically below the receiving portion to discharge the liquid droplet containing the predetermined amount of cells that has fallen down due to gravity toward the target portion. The sensing unit may be a digital camera. The digital camera may be fixed at a predetermined distance from the upper surface of the liquid droplet manipulation unit and have a lens suitable for close-up shot of the liquid droplet manipulation unit.

The control unit includes a microprocessor and is driven by a software including a quantitative analysis module analyzing the number of cells contained in each liquid droplet within the liquid droplet manipulation unit using a signal inputted from the sensing unit, and a liquid droplet manipulation module generating a control signal to allow the liquid droplet manipulation unit to perform operations of dividing a liquid droplet, transferring, and merging liquid droplets and to finally exhaust a plurality of liquid droplets each containing a desired number of cells. The quantitative analysis module may perform quantitative analysis of each liquid droplet whenever arrangement of the liquid droplets is varied under control of the liquid droplet manipulation module.

The dispensing unit of the quantitative cell dispensing apparatus using the liquid droplet manipulation may include: an electric field generating electrode having a vertically long syringe needle shape, an upper end connected with the liquid droplet outlet portion, an inside constituting a receiving portion receiving liquid droplets containing a cell, and a lower end where a dispensing port is formed; a target plate grounded and located below the electric field generating electrode to support a target portion that corresponds to the dispensing port; and an open type voltage applying device applying a predetermined voltage to the electric field generating electrode to allow a liquid droplet containing a cell to be discharged to the target portion by Coulomb force originated from charges concentrated on the dispensing port and the target portion.

Here, cells entering the receiving portion through the upper end of the electric field generating electrode fall down mainly due to gravity and are concentrated on the dispensing port, and contained in a liquid droplet and discharged during a liquid droplet discharge operation using electric charge concentration.

Electrowetting used in the liquid droplet manipulation unit means a phenomenon that a contact angle of a liquid droplet changes when a liquid droplet of a polar fluid is provided on an electrode coated with an insulation layer and a voltage is applied to the electrode. In a narrow sense, the electrowetting means a phenomenon that a contact angle with respect to the insulation layer decreases and so a liquid droplet spreads when an external electric potential of the liquid droplet gets high. A technology of controlling micro-fluidic movements using electrowetting has been proposed through a plurality of papers (An investigation of electrowetting-based microactivation, July/August 1990, Colgate, Matsumoto: J. Vac. Sci. Technol. A vol. 8#4 p. 3625-3633. Electrostatic activation of liquid droplets for microreactor applications, July/August 1998, Washizu: IEEEtrans. on Ind. App. v. 34, #4, pp. 732-737).

At this point, a contact angle of a liquid crystal is given by Equation 1 of Lippomann-Young.

$$\cos\theta = \cos\theta_0 + \frac{\varepsilon}{2\gamma_{LG}} \frac{V^2}{d} \quad \text{Equation 1}$$

where $\theta_0$ is a contact angle when an external voltage is 0 V, $\gamma_{LG}$ is surface tension of a liquid boundary surface, V is an external voltage, $\varepsilon$ and d are a dielectric constant and a thickness of an insulation layer, respectively. According to Equation 1, a small contact angle may be obtained when the thickness of the insulation layer is small or the applied external voltage is high. However, these two requirements causes dielectric breakdown. There is a limitation in making a thin thickness of an insulation layer, and a critical voltage Vc where a contact angle does not reduce any more and dielectric breakdown occurs appears at a predetermined voltage as an external voltage is raised continuously. This critical voltage Vc means that there is a limitation in variation of a contact angle between a liquid droplet and an insulation layer caused by electrowetting. This also means that a liquid droplet manipulation ability of a liquid droplet manipulation apparatus using electrowetting may depend on a size of the critical voltage Vc.

A liquid droplet manipulation unit of a quantitative cell dispensing apparatus according to the present invention moves a liquid droplet containing a relatively large and heavy cell. Electrolyte is added to hydrophilic suspension containing a plurality of cells. The adding of electrolyte raises a maximum external voltage that can be applied for manipulation of a liquid droplet of the suspension, that is, a critical voltage Vc, and thus increases variation in a contact angel between the liquid droplet and the insulation layer. Also, a speed at which the contact angle changes is improved. These advantages allow the liquid droplet manipulation unit to swiftly divide, transfer, and merge liquid droplets of hydrophilic suspension containing a plurality of cells in high speed.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. In the drawings, the thicknesses of layers and regions are exaggerated for clarity. Like reference numerals in the drawings denote like elements.

Figure 1:
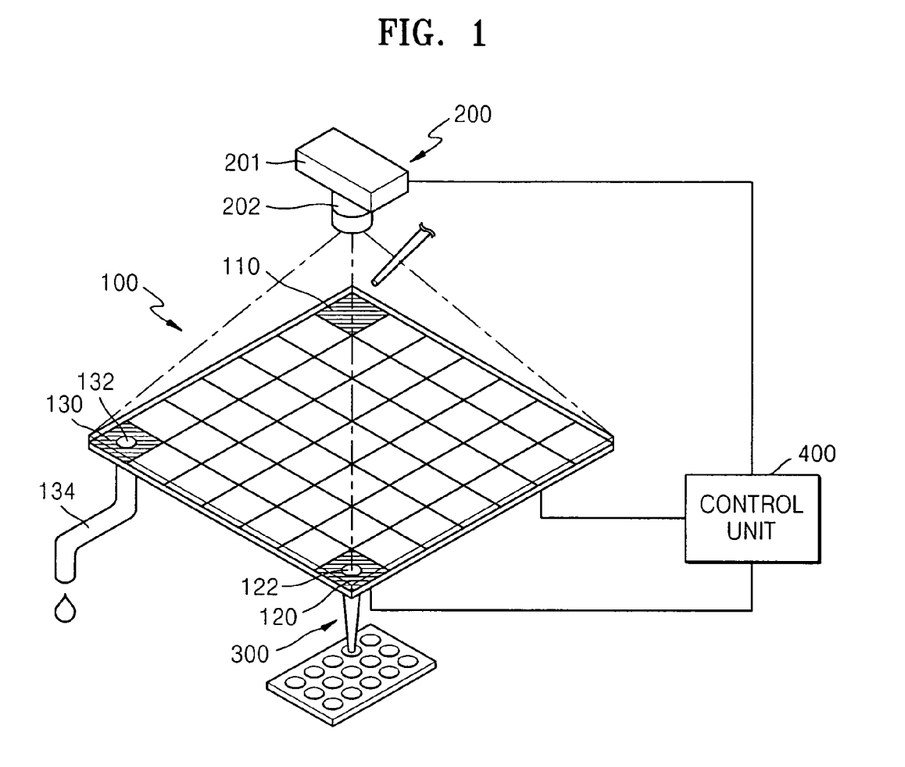
FIG. 1 is a schematic perspective view of a quantitative cell dispensing apparatus using liquid droplet manipulation according to an embodiment of the present invention.

FIG. 1 is a schematic perspective view of a quantitative cell dispensing apparatus using liquid droplet manipulation according to an embodiment of the present invention. The quantitative cell dispensing apparatus includes a liquid droplet manipulation unit 100 using electrowetting; a sensing unit 200 located to face a liquid droplet manipulation surface of the liquid droplet manipulation unit 100; a dispensing unit 300 connected to a liquid droplet outlet portion 120 of the liquid droplet manipulation unit 100; and a control unit 400 controlling the units.

The liquid droplet manipulation unit 100 includes an electrode array consisting of a plurality of electrode pads. An inlet 110 and at least one liquid droplet outlet portion 120 are formed in the electrode array. The inlet 110 supplies hydrophilic suspension containing a plurality of cells, and the liquid droplet outlet portion 120 exhausts a droplet containing a cell quantitatively processed through manipulation such as division, transfer, and merging. The liquid droplet manipulation unit 100 has a structure that provides a predetermined space between a lower substrate and an upper substrate in order to allow liquid droplet manipulation. The inlet 110 is formed by partially cutting the upper substrate or by extending the lower substrate where the electrode pads are provided to the outside of the upper substrate such that the inlet 110 is open upward. An electrode pad that corresponds to the liquid droplet outlet portion 120, that is, a liquid droplet pad has a structure allowing a liquid droplet that has reached a space above the liquid droplet pad to be exhausted to the outside. For example, the liquid droplet may have an exhaust port 122 pierced downward. The exhaust port 122 is connected to the dispensing unit 300. Besides the above-described structure, variety of structures connecting the liquid droplet outlet portion 120 with the dispensing unit 300 may be provided as far as the structures can exhaust a liquid droplet from the space to the outside using electrowetting and gravity.

The liquid droplet manipulation unit 100 may include at least one drain portion 130. The drain portion 130 includes an electrode pad (i.e., a drain pad) that corresponds to the drain portion 130, and a drain passage 134 connecting the space above the drain pad with the outside. The drain pad may be connected with the drain passage 134 through a drain hole 132 formed in the center of the drain pad. The drain portion 130 allows unnecessary liquid droplets not containing a cell to be exhausted to the outside during operation of the liquid droplet manipulation unit 100.

The sensing unit 200 is located to face a liquid droplet manipulation surface of the liquid droplet manipulation unit 100 to optically sense the number of cells contained in each of liquid droplets distributed on the electrode array. The sensing unit 200 may be a digital camera 201. The digital camera 201 is fixed at a predetermined distance from an upper surface of the liquid droplet manipulation unit 100 and may include a lens 202 appropriate for a close-up shot of an entire surface of the liquid droplet manipulation unit at the predetermined distance. The digital camera 201 converts an image formed by the lens 202 into a digital signal using an image sensor such as charged coupled devices (CCDs) and complementary metal oxide semiconductor (CMOS) sensors, and delivers the digital signal to the control unit 400.

The control unit 400 analyzes a signal inputted from the sensing unit 200 to count the number of cells contained in each liquid droplet captured, applies a control signal to the liquid droplet manipulation unit 100 until liquid droplets containing a desired number of cells are obtained, and divides, transfers, and merges the liquid droplets repeatedly and selectively. The control unit 400 may be one of an exclusive operation unit including a microprocessor and a general-purpose computer performing a task using software including a quantitative analysis module and a liquid droplet manipulation module.

The dispensing unit 300 includes a receiving portion connected with the liquid droplet outlet pad to receive liquid droplets containing a predetermined amount of cells, and a dispensing port located vertically below the receiving portion to discharge the liquid droplets containing the predetermined amount of cells that has fallen down due to gravity to a target portion. A variety of devices may be adopted to discharge a liquid droplet. For example, a device may use electric charge concentration. In this case, the dispensing unit 300 is also connected to the control unit 400 and operates according to a control signal from the control unit 400.

Hydrophilic suspension containing a plurality of cells includes electrolyte. One material selected from the group consisting of halogenide of alkali metal, alkali metal sulfate, and alkali metal nitrate may be added as the electrolyte. The addition of the electrolyte increases a critical voltage Vc applied to each electrode pad for liquid droplet manipulation by the liquid droplet manipulation unit 100, and thus liquid droplet manipulation characteristics including mobility and reaction speed of a liquid droplet improve.

Figure 2:
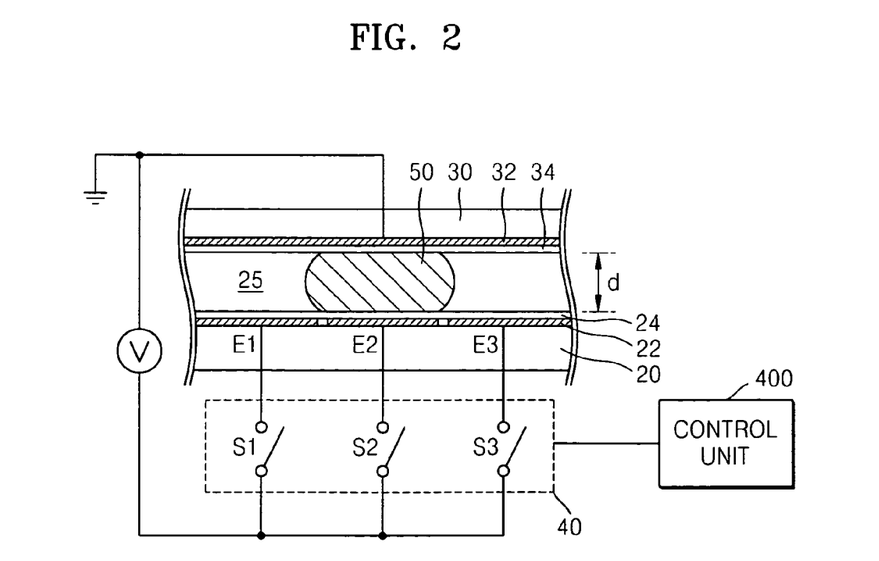
FIG. 2 is a schematic cross-sectional view of a liquid droplet manipulation unit according to an embodiment of the present invention.

FIG. 2 is a schematic cross-sectional view of a liquid droplet manipulation unit according to an embodiment of the present invention. The liquid droplet manipulation unit 100 includes a lower substrate 20, and a transparent upper substrate 30 located a predetermined distance d from the lower substrate 20 to face an upper surface of the lower substrate 20 and substantially in parallel to the lower substrate 20 to provide a predetermined space 25 between the upper substrate 30 and the lower substrate 20. An electrode array consisting of a plurality of electrode pads 22 (E1, E2, E3, . . . ) electrically separated from one another is provided on an upper surface of the lower substrate 20, and a first film 24 having insulation property and hydrophobicity is provided on an upper surface of the electrode array. The upper substrate 30 and structures provided on a lower surface of the upper substrate 30 are all formed of transparent materials to allow a liquid droplet 50 existing in the space 25 to be projected on an upper surface of the upper substrate 30. Transparent electrodes 32 are provided on the lower surface of the upper substrate 30, and a transparent and hydrophobic second film 34 is provided on a surface of the transparent electrode 32 contacting the space. Also, an electrode selection portion 40 connected to each of the plurality of electrode pads 22 (E1, E2, E3, . . . ) is provided to select some of the electrode pads 22 constituting the electrode array and apply a predetermined voltage thereto.

Here, the first film 24 may be one of an insulation layer formed of Parylene C™ or a metal oxide, and a hydrophobic layer such as Teflon AF 1600™. The transparent electrode 32 may be formed of a transparent conductive material such as indium-tin-oxide (ITO) and integrally formed over an entire surface of the upper substrate 30. The electrode selection portion 40 may include a plurality of switching devices S1, S2, S3, ... connected to the plurality of electrode pads 22 (E1, E2, E3, ... ), respectively. The space 25 is filled with non-polar fluid. The non-polar fluid may be air or oil fluid preventing the hydrophobic liquid droplet 50 from evaporating.

Figure 3:
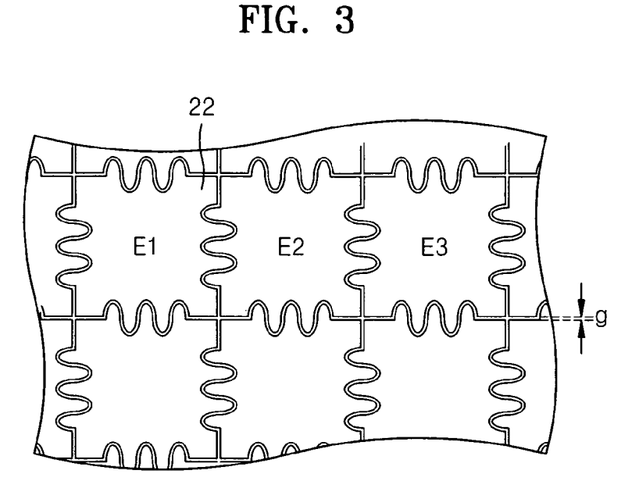
FIG. 3 is a plan view illustrating portion of an electrode array of the liquid droplet manipulation unit illustrated in FIG. 2.

FIG. 3 is a plan view illustrating portion of an electrode array of the liquid droplet manipulation unit illustrated in FIG. 2. The plurality of electrode pads are arranged with an insulation gap g interposed therebetween. Each of the plurality of electrode pads has an unevenness formed in its edge and thus is engaged with adjacent electrode pads to allow a liquid droplet to swiftly move between the electrode pads.

Figure 4:
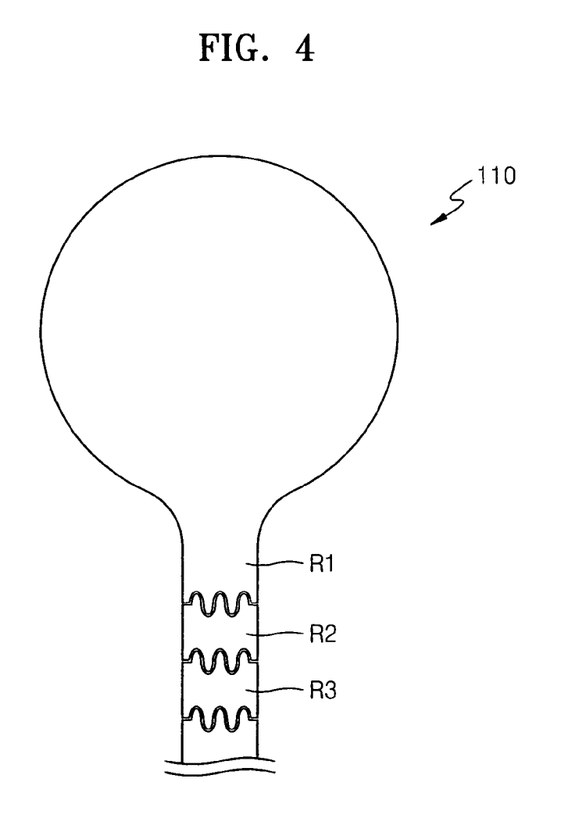
FIG. 4 is a plan view illustrating an inlet of a liquid droplet manipulation unit according to an embodiment of the present invention.

FIG. 4 is a plan view illustrating an inlet of a liquid droplet manipulation unit according to an embodiment of the present invention. The inlet 110 may include a first inlet electrode R1 having a large area in order to store a large amount of hydrophilic suspension. The first inlet electrode R1 has a narrow exit. A second inlet electrode R2 and a third inlet electrode R3 having a narrow width, respectively, are formed in the exit of the first inlet electrode R1.

When a voltage is applied to the second and third inlet electrodes R2 and R3, a surface of a liquid droplet takes on hydrophilicity, so that a liquid droplet on the first inlet electrode R1 extends up to the third inlet electrode R3. With this state, when a voltage applied to the second inlet electrode R2 is cut off, a surface of the second inlet electrode R2 takes on hydrophobicity, so that the liquid droplet is divided into two portions, and a small-sized liquid droplet is located on the third inlet electrode R3. The inlet 110 can divide the hydrophilic suspension into liquid droplets of a manipulation-easy size and supply the divided liquid droplets.

Figure 5:
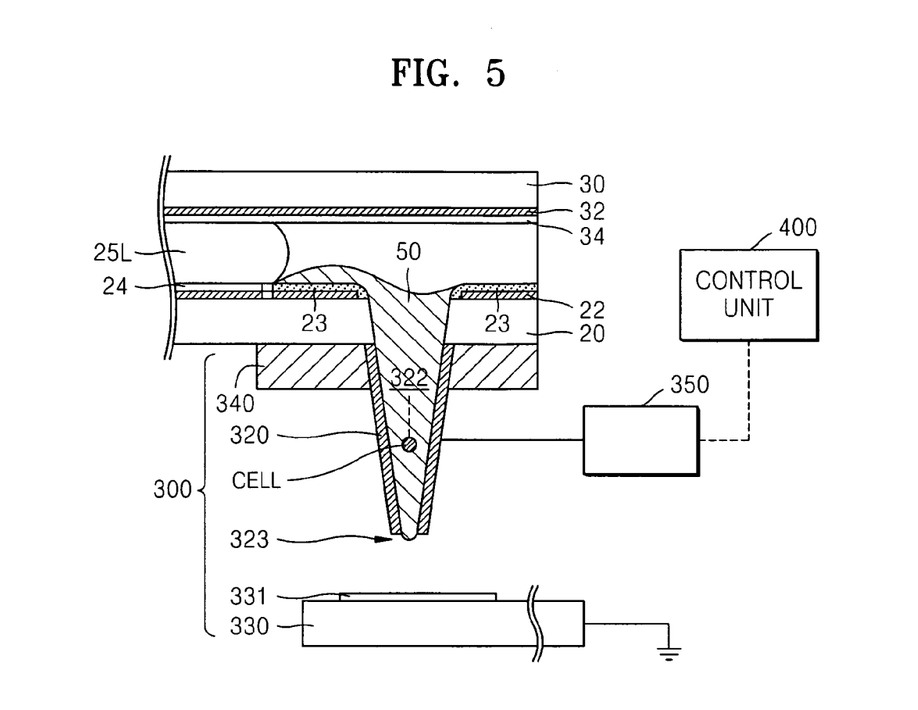
FIG. 5 is a cross-sectional view of a liquid droplet outlet portion of a liquid droplet manipulation unit and a dispensing unit according to an embodiment of the present invention.

FIG. 5 is a cross-sectional view of a liquid droplet outlet portion of a liquid droplet manipulation unit and a dispensing unit according to an embodiment of the present invention. FIG. 5 shows the liquid droplet outlet portion 120 provided to one end of the liquid droplet manipulation unit illustrated in FIG. 1 and the dispensing unit 300 connected to the liquid droplet outlet portion 120. An exhaust port is provided in an electrode pad 22 (i.e., a liquid droplet outlet pad) that corresponds to the liquid droplet outlet portion 120. A hole communicating with the exhaust port is formed in the lower substrate 20. The dispensing unit 300 using electric charge concentration is located below the hole.

According to the present embodiment, the space inside the liquid droplet manipulation unit is filled with oil fluid 25L, and an upper surface of the liquid droplet outlet pad is maintained to always take on hydrophilicity so that the oil fluid 25L may not intrude into the upper surface of the liquid droplet outlet pad. Therefore, an insulation layer 23 hydrophilic-surface processed or formed of a hydrophilic material may be located on an upper surface of the liquid droplet outlet pad. On the other hand, of course, a predetermined voltage is constantly applied to the liquid droplet outlet pad to maintain hydrophilicity. The hydrophilic suspension 50 that has come from the oil fluid 25L and entered the liquid droplet outlet pad moves to the dispensing unit 300 through the dispensing port.

The dispensing unit 300 according to the present embodiment includes an electric field generating electrode 320 of a vertically long syringe needle shape, a target plate 330 grounded and located below the electric field generating electrode 320, and an open type voltage applying device 350 applying a predetermined voltage to the electric field generating electrode 320. The electric field generating electrode 320 has an upper end connected with the liquid droplet outlet portion, specifically, the exhaust port provided in the liquid droplet outlet pad. The inside of the electric field generating electrode 320 constitutes a receiving portion 322 receiving a liquid droplet containing a cell, and a dispensing port 323 is provided to the lower end of the electric field generating electrode 320. A target portion 331 is provided on an upper surface of the target plate 330 to face the dispensing port 323.

When a cell surrounded by a liquid droplet is supplied to the receiving portion 322, the cell vertically falls down mainly due to gravity and moves to the dispensing port 323. After that, when the open type voltage applying device 350 applies a voltage to the electric field generating electrode 320, charges are concentrated on the dispensing port 323 and the target portion 331, and a liquid droplet containing a cell is discharged by Coulomb force originating from the concentrated charges. The open type voltage applying device 350 may be controlled by the control unit 400. The open type voltage applying device 350 may apply a DC voltage and an AC voltage simultaneously to the electric field generating electrode 320. The intensity and frequency of the voltage may be controlled by the control unit depending on conditions such as a size of a cell to be discharged.

The electric field generating electrode 320 may be formed of various conductive materials such as metal (Au, Pt, Cu, and etc.), a conductive polymer, and ITO glass. The dispensing unit 300 includes a support member 340 supporting the electric field generating electrode 320. The support member 340 may be fixed in a portion of the liquid droplet manipulation unit 100, e.g., a portion of the lower substrate 20 that corresponds to the liquid droplet outlet portion.

The dispensing port 323 is connected with the receiving portion 322 and provided below the receiving portion 322. Since an inner diameter of the dispensing port 323 is very small, the suspension 50 overcomes gravity with its surface tension and hangs on the dispensing port 323 unless external force is applied. Vicinity of the dispensing port 323 is hydrophobic-processed, which increases a contact angle of the suspension 50 to prevent the suspension 50 from flowing sideways from the dispensing port 323.

The target plate 330 constitutes a cell chip and may be formed of one material selected from the group consisting of silicon, glass, and polymer. In the present embodiment, the target plate 330 is formed of silicon. The target plate 330 is located below the electric field generating electrode 320 and is roughly perpendicular to the electric field generating electrode 320. The target portion 331 provided on the target plate 330 is coated with a material fixing a cell discharged from the dispensing port 323. Also, though not shown in the drawings, a plurality of target portions 331 may be provided on the target plate 330. In this case, the target plate 330 may be relatively moved with respect to the dispensing port 323 to allow a cell to be sequentially discharged onto the plurality of target portions 331.

Figure 6:
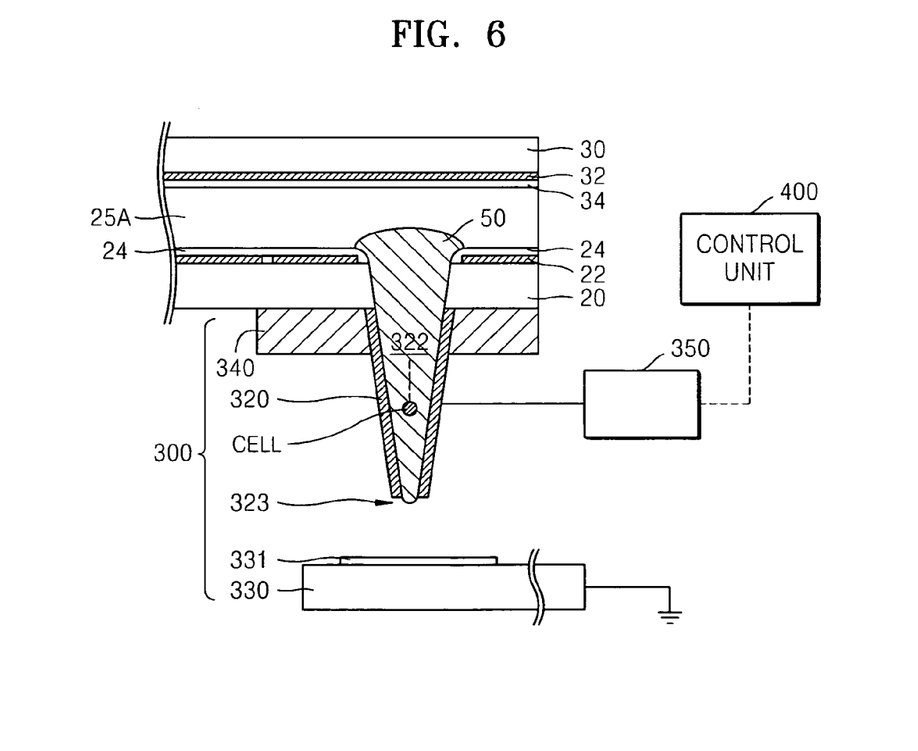
FIG. 6 is a cross-sectional view of a liquid droplet outlet portion of a liquid droplet manipulation unit and a dispensing unit according to another embodiment of the present invention.

FIG. 6 is a cross-sectional view of a liquid droplet outlet portion of a liquid droplet manipulation unit and a dispensing unit according to another embodiment of the present invention. Another embodiment is mostly the same as the embodiment illustrated in FIG. 5. Only difference is that a first film having insulation property and hydrophobicity is formed also on an upper surface of the liquid droplet outlet pad of the liquid droplet outlet portion like other portions of an upper surface of the electrode array. In this case, a space inside of a liquid droplet manipulation unit is filled with air 25A.

Figure 7:
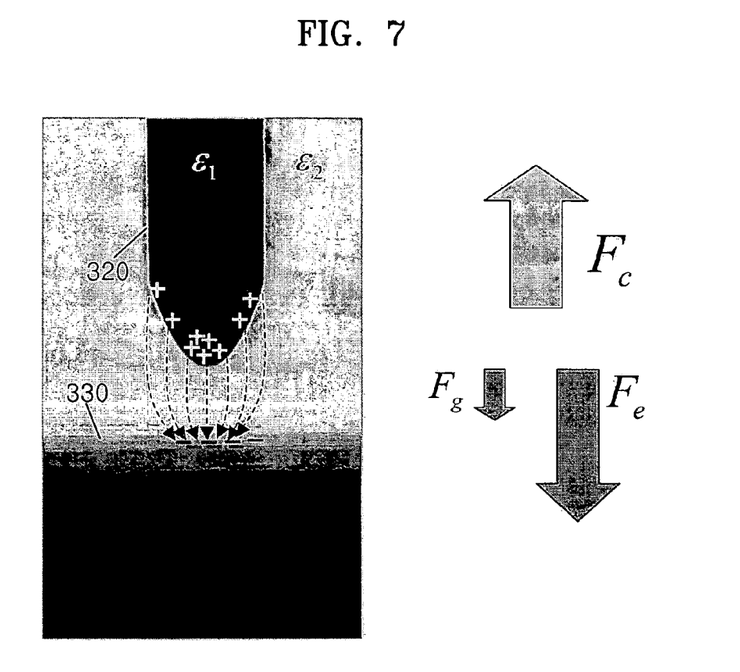
FIG. 7 is a view illustrating a liquid droplet discharging principle of the dispensing unit illustrated in FIGS. 5 and 6.
Figure 8:
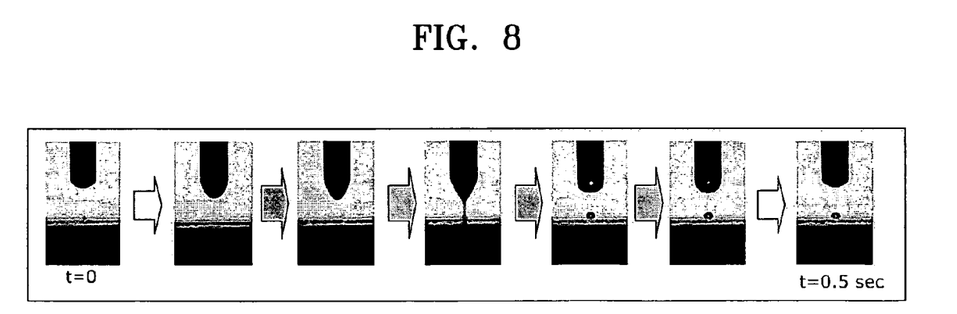
FIG. 8 is a view illustrating a liquid droplet discharging process of the dispensing unit illustrated in FIGS. 5 and 6.

Principle and process by which a liquid droplet is discharged from the dispensing unit 300 illustrated in FIGS. 5 and 6 with the help of electric charge concentration will be described below. FIG. 7 illustrates a liquid droplet discharging principle of the dispensing unit illustrated in FIGS. 5, 6, and 8 illustrates a liquid droplet discharging process of the dispensing unit illustrated in FIGS. 5 and 6.

When the open type voltage applying device 350 applies a voltage to the electric field generating electrode 320, a surface of the suspension 50 hanging on the dispensing port 323 is charged with a positive charge, which induces a negative charge on the substrate 330 (specifically, the target portion 331). Therefore, an electric field is formed between the positive charge and the negative charge as illustrated by a dotted line of FIG. 7.

It is known that gravitational force $F_g$, surface tension $F_c$, and Coulomb force $F_e$ act on a liquid droplet hanging on the dispensing port 323. Also, since the gravitational force $F_g$, surface tension $F_c$, and Coulomb force act in an arrow direction of FIG. 7, the gravitational force $F_g$, surface tension $F_c$, and Coulomb force right before the liquid droplet falls down satisfy Equation 1 below and maintains equilibrium relation.

Gravitational force $F_g$+Coulomb force $F_e$=surface tension $F_c$    Equation 1, where gravitational force $F_g = \rho g \Delta V^{drop}$ ($\rho$ is density of a liquid droplet, g is gravitational acceleration, $\Delta V^{drop}$ is a volume of a liquid droplet hanging on a dispensing port), surface tension $F_c = 2\pi\gamma R$ (R is a radius of a dispensing port, $\gamma$ is a surface tension per unit length), Coulomb force $Fe = \rho_f E - E^2 \nabla \epsilon / 2$ ($\rho_f$ is a free charge of a liquid droplet, E is intensity of an electric field, and $\nabla \epsilon$ is permittivity). Here, electric force is represented by sum of electrophoresis force $\rho_f E$ and dielectrophoresis force $-E^2 \nabla \epsilon / 2$. In Equation 1, since the gravitational force $F_g$ is proportional to the volume of a liquid droplet hanging on the dispensing port and the volume of this liquid droplet is very small, the gravitational force $F_g$ can be ignored.

Therefore, when Coulomb force $F_e$ greater than the surface tension $F_c$ of the liquid droplet hanging on the dispensing port 323 is generated, the equilibrium relation of Equation 1 is destroyed by this Coulomb force, and thus the liquid droplet can fall down to the target portion of the target plate 330. Particularly, since most of charges are concentrated on the lower end of the liquid droplet's surface and strong electrophoresis force acts on the lower end, a liquid droplet of a small size may effectively fall down.

A liquid droplet discharging process will now be described in more detail with reference to FIG. 8. After the suspension is supplied to the inside of the receiving portion 322, the open type voltage applying device 350 applies a voltage to the electric field generating electrode 320 as described above. When a voltage having superposition of a DC component of 5-100 kV and an AC component of 5-100 kV with a frequency of 10-1 kHz is applied to the electric field generating electrode 320, the liquid droplet hanging on the dispensing port 323 is charged with positive charges, and thus negative charges are induced on the grounded target plate. At this point, a DC component of 500-10 kV and AC component of 500-10 kV having a frequency of 10-1 kHz may be simultaneously applied. When a voltage including a DC component and an AC component deviating from the above-described voltage range and frequency range is applied, Coulomb force excessively decreases or increases, so that the liquid droplet may not effectively fall down. Most desirably, a voltage having superposition of a DC component of 2 kV and an AC component of 500V with a frequency of 130 Hz may be applied to the electric field generating electrode 320.

The Coulomb force is concentrated on the lower portion of the liquid droplet of a bio molecule. Also, the liquid droplet that has hung on the dispensing port 323 by the Coulomb force flows down to the target plate 330 and takes on an about pot shape as illustrated in the center photo of FIG. 8. A neck is formed in the pot-shaped liquid droplet. When the liquid droplet flows down to the target plate 330 as the neck becomes narrow, the positive charges contained in the liquid droplet vanish together with the negative charges of the substrate 330 (i.e., target plate 331). Therefore, the Coulomb force drawing downward the liquid droplet that has hung on the dispensing port 323 reduces. Not only the charges with which the liquid droplet has been charged vanish and thus the Coulomb force thereof reduces, but also the surface tension of the liquid droplet acts in both directions around the neck, so that the liquid droplet is divided into two portions. Therefore, the liquid droplet falls down and sticks on the substrate 330 as illustrated in a last photo of FIG. 8.

At this point, since cells contained inside hydrophilic suspension fall down due to gravity within the electric field generating electrode 320 and are concentrated on the lower end of the liquid droplet hanging on the dispensing port, the cells are discharged together with the liquid droplet and stick on the substrate 330.

Figure 9A:
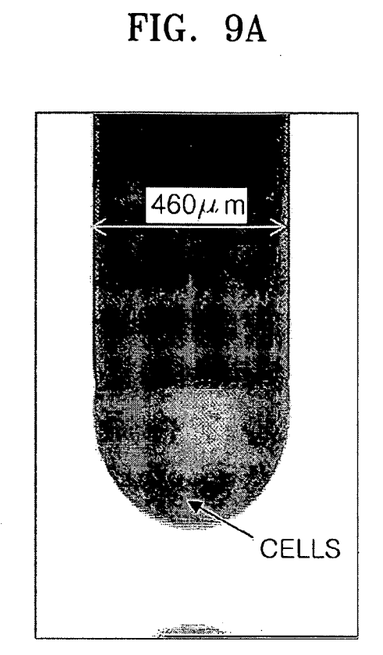
FIGS. 9A and 9B are photos illustrating suspension of cells is discharged using the dispensing unit illustrated in FIGS. 5 and 6.
Figure 9B:
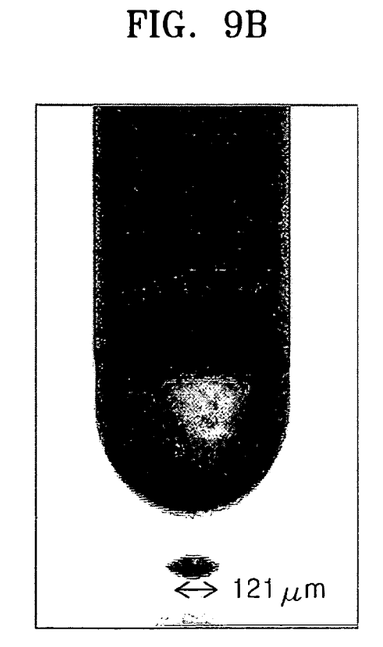

FIGS. 9A and 9B are photos illustrating suspension of cells is discharged using the dispensing unit illustrated in FIGS. 5 and 6. A liquid droplet of suspension hangs on the dispensing port having a diameter of 460 μm. A plurality of cells contained in the liquid droplet are concentrated adjacently on the surface of the liquid droplet. While portion of the liquid droplet is separated, the cells are simultaneously discharged as illustrated in FIG. 9B.

Figure 10A:
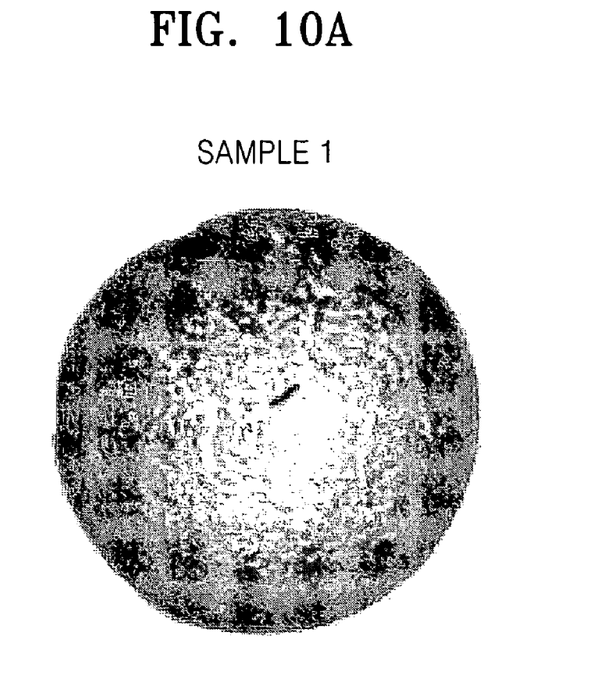
FIGS. 10A and 10B are photos illustrating a liquid droplet discharged by the dispensing unit illustrated in FIGS. 5 and 6.
Figure 10B:
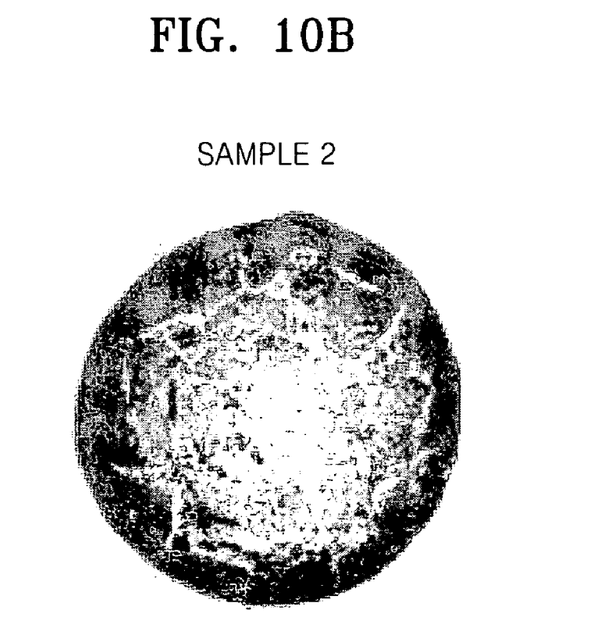

FIGS. 10A and 10B are photos illustrating a liquid droplet discharged by the dispensing unit illustrated in FIGS. 5 and 6. Cells are dyed with Trypan blue and discharged from suspension having density of $4.0 \times 10^5$ cells/ml. Checking whether the discharged cells are alive shows that nineteen cells of FIG. 10A have all survived and thirty cells of thirty one cells in FIG. 10B have survived. Repeatedly checking in this manner reveals that a survival rate has been about 94%. In view of a fact that a survival rate of cells that has not passed through a discharge, process is 95%, it is confirmed, that the liquid droplet dispensing unit of the quantitative cell dispensing apparatus according to the present invention does not have an influence on the survival of the cells.

On the other hand, electrolyte is added to the hydrophilic suspension containing cells in the quantitative cell dispensing apparatus according to the present invention. Influence of the adding of the electrolyte on the quantitative cell dispensing apparatus will now be described with reference to FIG. 9 through 12. In detail, influence on cell transfer ability of the liquid droplet manipulation unit will be described.

Figure 11:
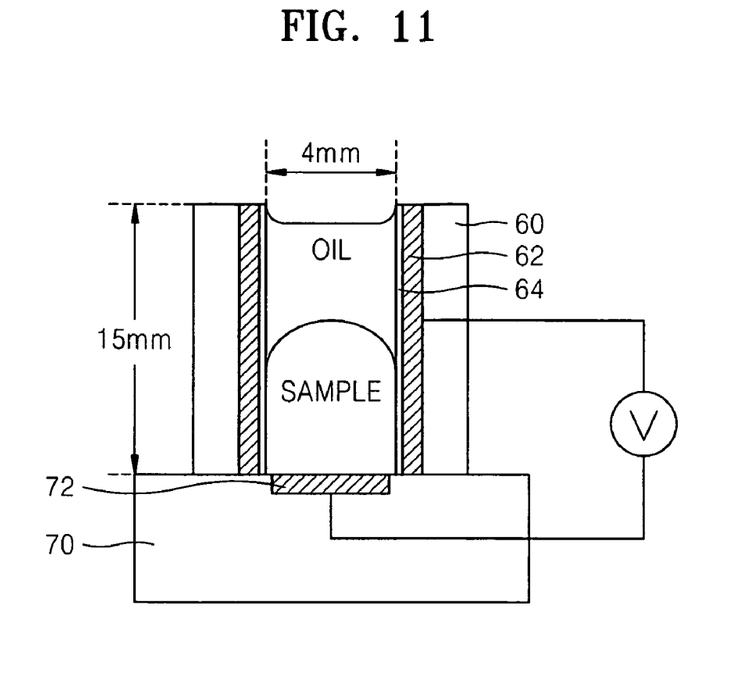
FIG. 11 is a cross-sectional view illustrating an example of experiment apparatus for measuring a change in a contact angle caused by electrowetting and a critical voltage.

FIG. 11 is a cross-sectional view illustrating an example of experiment apparatus for measuring a change in a contact angle caused by electrowetting and a critical voltage. In the experiment apparatus, an ITO thin film is deposited on a glass plate 70 to form a reference electrode 72, and a glass tube 60 having a diameter of 4 mm and a length of 15 mm is vertically installed on the reference electrode 72. An ITO electrode 62 is provided in an inner wall of the glass tube 60, and an insulation layer 64 is provided on a surface of the ITO electrode 62. The voltage applying device is connected to the ITO electrode. Parylene C™ having excellent optical transparency and biocompatibility, having a thickness of 2.5 μm, and whose surface has hydrophobicity is used for the insulation layer 64.

PBS (1 mM sodium phosphate, 15 mM NaCl, pH 7.4) has been injected as sample solution into the experiment apparatus, and oil has been injected over the sample solution to prevent evaporation of the solution. An experiment has been performed while a voltage is gradually increased using the voltage applying device.

Figure 12A:
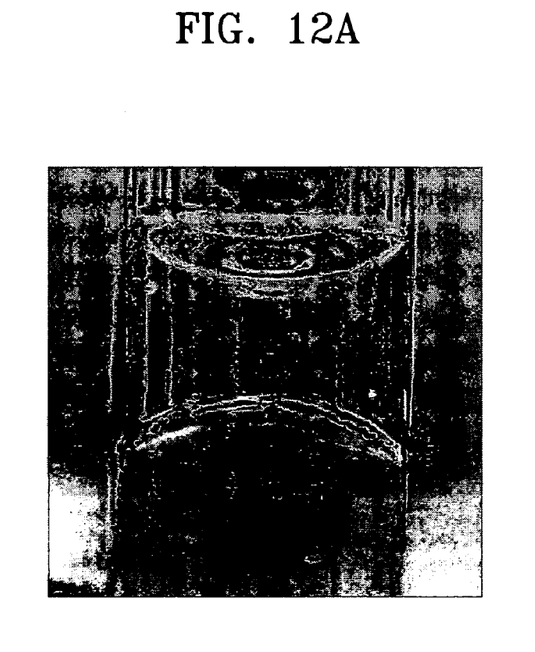
FIG. 12A through 12C are photos showing a change in a contact angle depending on a change in an external voltage having an influence on a sample solution.
Figure 12B:
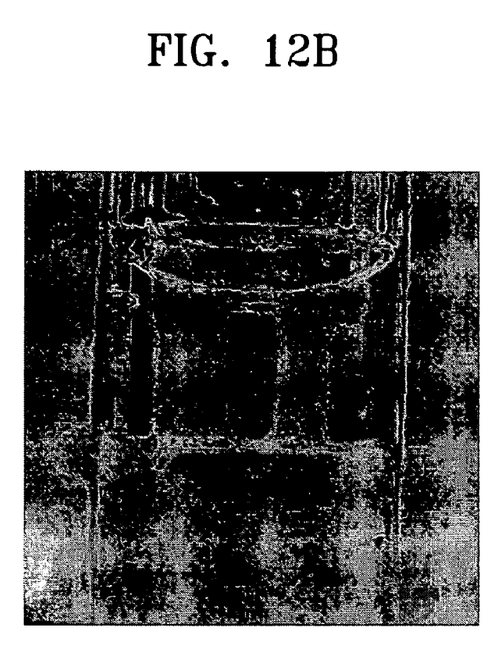
Figure 12C:
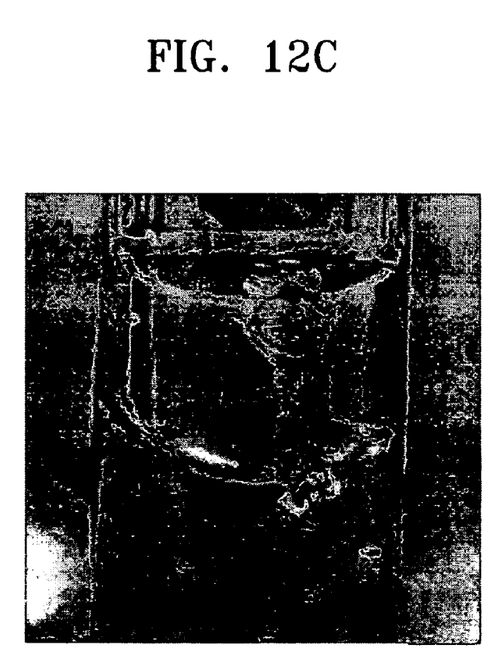

FIGS. 12A through 12C are photos showing a change in a contact angle depending on a change in an external voltage having an influence on a sample solution. FIG. 12A illustrates a state for a voltage zero where the insulation layer 64 takes on hydrophobicity, which increases a contact angle with respect to the sample solution, so that a boundary between the sample solution and the oil is convex in its center. FIG. 12B illustrates a state when a voltage smaller than a critical voltage Vc is applied to the ITO electrode 62. In this case, a contact angle between the sample solution and the insulation layer decreases, so that a boundary therebetween is nearly flat. FIG. 12C illustrates a state when a voltage greater than the critical voltage Vc is applied to the ITO electrode. In this case, dielectric breakdown occurs and sparks and air bubbles are generated.

Figure 13:
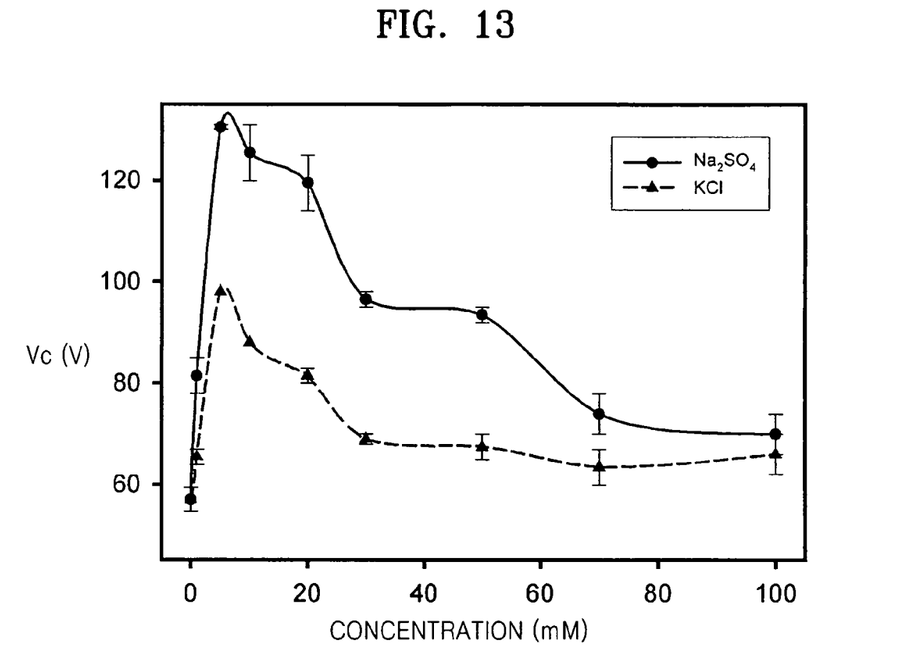
FIG. 13 is a graph illustrating a critical voltage Vc vs. electrolyte density of a sample solution in an experiment performed by the experiment apparatus illustrated in FIG. 11.

FIG. 13 is a graph illustrating a critical voltage Vc vs. electrolyte density of a sample solution in an experiment performed by the experiment apparatus illustrated in FIG. 11. A critical voltage Vc before electrolyte is added to the sample solution is about 60 V, but a critical voltage has been raised to 80 V and 110 V as $Na_2SO_4$, which is ternary electrolyte, is added as much as densities of 1 mM and 5 mM, respectively. Also, a critical voltage has been raised to 65 V and 90 V as KCl, which is binary electrolyte, is added as much as densities of 1 mM and 5 mM. Also, examination of a change pattern of the critical voltage shows that the critical voltage has a maximum value in each electrolyte's density range of about 5-10 mM. When each electrolyte's density exceeds the above density range, the critical voltage tends to decreases again.

Figure 14:
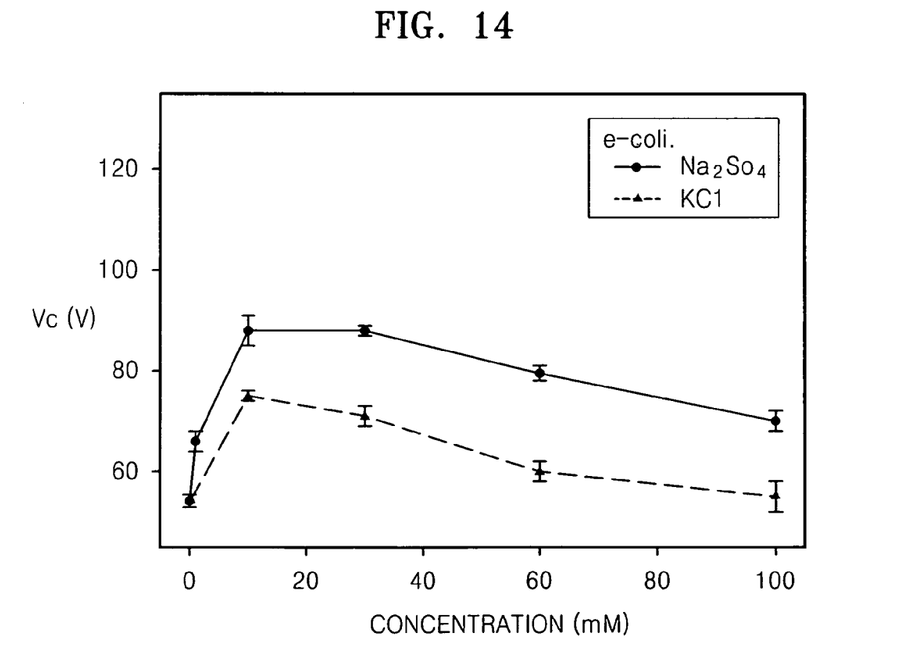
FIG. 14 is a graph illustrating a critical voltage Vc vs. electrolyte density of a sample solution containing *E. coli* in an experiment performed by the experiment apparatus illustrated in FIG. 11.

FIG. 14 is a graph illustrating a critical voltage Vc vs. electrolyte density of a sample solution containing a coli in the experiment performed by the experiment apparatus illustrated in FIG. 11. It has been shown that a critical voltage is raised due to addition of electrolyte even for a case of suspension containing a cell, which is a non-polar particle (e.g., e-coli). A higher critical voltage is achieved when electrolyte's density is in a range of 1-100 mM rather than zero mM. The suspension containing cells shows a smoother change characteristic for a critical voltage versus electrolyte's density compared to the sample solution not containing cells. When the electrolyte's density is in a range of 10-30 mM, rise of the critical voltage is most conspicuous.

As described above, the rise of the critical voltage increases a change in a liquid droplet's contact angle in the liquid droplet manipulation apparatus using electrowetting and allows transfer of an animal cell which is relatively heavy compared to bio materials such as DNA and protein.

A strong electrolyte may be effectively used for an electrolyte to be added to hydrophilic suspension of cells in the apparatus according to the present invention. When having a high degree of ionization, an electrolyte swiftly delivers electricity. Such an electrolyte is called a strong electrolyte. An opposite one is called a weak electrolyte. For example, halogenide of alkali metal, salt such as oxoacid salt originated from reaction between a strong acid and a strong base, and a strong acid and a strong base themselves serve as a strong electrolyte. Since a strong acid or a strong base itself may have an influence on survival of a cell, halogenide of alkali metal, alkali metal sulfate, or alkali metal nitrate are suitable for an electrolyte.

The quantitative cell dispensing apparatus using liquid droplet manipulation dispenses suspension of cells in liquid droplets having a minute volume, simultaneously allows each liquid droplet to contain a predetermined amount of cells, and provides the quantitatively dispensed liquid droplets to the target portion, which improves uniformity of a cell chip and enhances productivity.

Also, the apparatus of the present invention does not include a moving member and can be miniaturized. Also, a series of processes performed inside the apparatus can be electrically controlled.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A quantitative cell dispensing apparatus using liquid droplet manipulation, the apparatus comprising:
   a hydrophilic suspension containing a plurality of cells and an electrolyte;
   a liquid droplet manipulation unit configured to manipulate a plurality of liquid droplets of the hydrophilic suspension, the liquid droplet manipulation unit comprising:
      a lower substrate;
      a transparent upper substrate;
      a predetermined space disposed between the lower substrate and the transparent upper substrate, and containing the hydrophilic suspension;
      an electrode array on the lower substrate and including a plurality of electrode pads electrically isolated from each other and on which the liquid droplets are manipulated;
      an inlet through which the hydrophilic suspension is supplied; and
      at least one liquid droplet outlet portion configured to discharge the manipulated liquid droplets;
   a dispensing unit configured to discharge a liquid droplet of the plurality of liquid droplets received from the liquid droplet outlet portion to an outside of the dispensing unit;
   a sensing unit configured to optically sense the liquid droplets distributed on the electrode array of the liquid droplet manipulation unit; and
   a control unit configured to analyze a number of cells contained in each of the plurality of liquid droplets using a signal detected by the sensing unit and to control the liquid droplet manipulation unit to provide liquid droplets containing a predetermined number of cells to the liquid droplet outlet portion through dividing, transferring, and merging the liquid droplets; and
   an open type voltage applying device configured to apply a first predetermined voltage to allow liquid droplets containing a cell to be discharged to the outside of the dispensing unit by Coulomb force.

2. The apparatus of claim 1, wherein the electrolyte is one material selected from the group consisting of halogenide of alkali metal, alkali metal sulfate, and alkali metal nitrate.

3. The apparatus of claim 2, wherein a concentration range of the electrolyte is 1-100 mM.

4. The apparatus of claim 1, wherein the liquid droplet manipulation unit further comprises at least one drain portion configured to drain a liquid droplet of the plurality of liquid droplets not containing a cell, disposed between the lower substrate and the transparent upper substrate, and having a drain pad corresponding to the drain portion and a drain passage connecting the drain portion above the drain pad with the outside of the dispensing unit.

5. The apparatus of claim 1, wherein the liquid droplet manipulation unit further comprises:
   a first film located on a surface of the electrode array and including an insulating, hydrophobic material;

the transparent upper substrate facing an upper surface of the lower substrate, and located substantially in parallel to the lower substrate such that the predetermined space is provided between the lower substrate and the upper substrate;

a transparent electrode located on a lower surface of the upper substrate;

a second film provided on a surface of the transparent electrode to contact the predetermined space and including a transparent, hydrophobic material;

a non-polar fluid filling the predetermined space; and an electrode selection portion connected to each of the plurality of electrode pads, and configured to select some of the electrode pads of the electrode array according to a control signal from the control unit to apply a second predetermined voltage thereto, wherein at least one electrode pad of the plurality of electrode pads is a liquid droplet outlet pad including an exhaust port.

6. The apparatus of claim 5, wherein the electrode array is arranged and formed such that each of the plurality of electrode pads has an unevenness formed in its edge and thus is engaged with adjacent electrode pads.

7. The apparatus of claim 5, wherein the non-polar fluid comprises air or oil.

8. The apparatus of claim 5, wherein the transparent electrode is integrally formed over an entire surface of the lower surface of the transparent upper substrate.

9. The apparatus of claim 5, wherein the dispensing unit comprises:
a receiving portion connected with the liquid droplet outlet pad to receive a liquid droplet containing a predetermined amount of cells; and
a dispensing port provided vertically below the receiving portion to discharge the liquid droplet containing the predetermined amount of cells that has fallen down due to gravity toward the outside of the dispensing unit.

10. The apparatus of claim 5, wherein the liquid droplet outlet pad has an upper surface covered with a layer including an insulating, hydrophilic material, and oil fluid is used for the non-polar fluid to prevent the non-polar fluid from penetrating a space above the liquid droplet outlet pad.

11. The apparatus of claim 5, wherein the plurality of electrode pads includes at least one drain pad including a drain hole, which is connected with a drain passage connecting the predetermined space with the outside of the dispensing unit.

12. The apparatus of claim 11, wherein the drain pad has an upper surface covered with a layer which including an insulating, hydrophilic material, and oil fluid is used for the non-polar fluid to prevent the non-polar fluid from penetrating a space above the drain pad.

13. The apparatus of claim 1, wherein the sensing unit comprises a digital camera.

14. The apparatus of claim 13, wherein the digital camera is fixed at a predetermined distance from an upper surface of the liquid droplet manipulation unit.

15. A quantitative cell dispensing apparatus using liquid droplet manipulation, the apparatus comprising:
a hydrophilic suspension containing a plurality of cells and an electrolyte;
a liquid droplet manipulation unit configured to manipulate a plurality of liquid droplets of the hydrophilic suspension the liquid droplet manipulation unit comprising:
a lower substrate;
a transparent upper substrate;
a predetermined space disposed between the lower substrate and the transparent upper substrate, and containing the hydrophilic suspension;
an electrode array on the lower substrate and including a plurality of electrode pads electrically isolated from each other and on which the liquid droplets are manipulated;
an inlet through which the hydrophilic suspension is supplied; and
at least one liquid droplet outlet portion configured to discharge the manipulated liquid droplets;
a dispensing unit configured to discharge a liquid droplet of the plurality of liquid droplets received from the liquid droplet outlet portion to a target portion outside of the dispensing unit;
a sensing unit configured to optically sense the liquid droplets distributed on the electrode array of the liquid droplet manipulation unit; and
a control unit configured to analyze a number of cells contained in each of the plurality of liquid droplets using a signal detected by the sensing unit and to control the liquid droplet manipulation unit to provide liquid droplets containing a predetermined number of cells to the liquid droplet outlet portion through dividing, transferring, and merging the liquid droplets,
wherein the dispensing unit of the quantitative cell dispensing apparatus using the liquid droplet manipulation includes:
an electric field generating electrode having a vertically long syringe needle shape, an upper end connected with the liquid droplet outlet portion, an inside constituting a receiving portion configured to receive liquid droplets containing a cell, and a lower end where a dispensing port is formed;
a target plate grounded and located below the electric field generating electrode to support the target portion that faces the dispensing port; and
an open type voltage applying device configured to apply a first predetermined voltage to the electric field generating electrode to allow liquid droplets containing a cell to be discharged to the target portion by Coulomb force originated from charges concentrated on the dispensing port and the target portion.

16. The apparatus of claim 15, wherein the dispensing unit further includes a support member which supports and surrounds an upper portion of the electric field generating electrode, and the support member is fixed in the liquid droplet manipulation unit.

17. The apparatus of claim 15, wherein the target plate is formed of one material selected from the group consisting of silicon, glass, and polymer.

18. The apparatus of claim 15, wherein the dispensing port of the electric field generating electrode includes a hydrophobic material.

19. The apparatus of claim 15, wherein the electrolyte is one material selected from the group consisting of halogenide of alkali metal, alkali metal sulfate, and alkali metal nitrate.

20. The apparatus of claim 19, wherein a concentration range of the electrolyte is 1-100 mM.

21. The apparatus of claim 15, wherein the liquid droplet manipulation unit further includes at least one drain portion configured to drain a liquid droplet not containing a cell, disposed between the lower substrate and the transparent upper substrate, and having a drain pad corresponding to the drain portion and a drain passage connecting the drain portion above the drain pad with the outside of the dispensing unit.

22. The apparatus of claim 15, wherein the liquid droplet manipulation unit further includes:
- a first film located on a surface of the electrode array and including an insulating, hydrophobic material;
- the transparent upper substrate facing an upper surface of the lower substrate, and located substantially in parallel to the lower substrate such that the predetermined space is provided between the lower substrate and the upper substrate;
- a transparent electrode located on a lower surface of the upper substrate;
- a second film provided on a surface of the transparent electrode to contact the predetermined space and including a transparent, hydrophobic material;
- a non-polar fluid filling the predetermined space; and
- an electrode selection portion connected to each of the plurality of electrode pads, and configured to select some of the electrode pads of the electrode array according to a control signal from the control unit to apply a second predetermined voltage thereto,
- wherein at least one electrode pad of the plurality of electrode pads is a liquid droplet outlet pad including an exhaust port.

23. The apparatus of claim 22, wherein the electrode array is arranged and formed such that each of the plurality of electrode pads has an unevenness formed in its edge and engaged with adjacent electrode pads.

24. The apparatus of claim 22, wherein the non-polar fluid comprises air or oil.

25. The apparatus of claim 22, wherein the transparent electrode is integrally formed over an entire surface of the lower surface of the transparent upper substrate.

26. The apparatus of claim 22, wherein the liquid droplet outlet pad has an upper surface covered with a layer which includes an insulating, hydrophilic material, and oil fluid is used for the non-polar fluid to prevent the non-polar fluid from penetrating a space above the liquid droplet outlet pad.

27. The apparatus of claim 26, wherein the plurality of electrode pads further includes at least one drain pad including a drain hole, which is connected with a drain passage connecting the space with the outside of the dispensing unit.

28. The apparatus of claim 22, wherein the plurality of electrode pads further includes at least one drain pad including a drain hole, which is connected with a drain passage connecting the space with the outside of the dispensing unit.

29. The apparatus of claim 28, wherein the drain pad has an upper surface covered with a layer which includes an insulating, hydrophilic material, and oil fluid is used for the non-polar fluid to prevent the non-polar fluid from penetrating a space above the drain pad.

30. The apparatus of claim 15, wherein the sensing unit comprises a digital camera.

31. The apparatus of claim 30, wherein the digital camera is fixed at a predetermined distance from the upper surface of the liquid droplet manipulation unit.

* * * * *